(12) United States Patent
Franiak-Pietryga et al.

(10) Patent No.: US 10,022,395 B2
(45) Date of Patent: *Jul. 17, 2018

(54) APPLICATION OF MALTOTRIOSE-COATED 4TH GENERATION POLY(PROPYLENEIMINE) DENDRIMER PPI-G4-OS-MAL-III

(71) Applicant: UNIWERSYTET LÓDZKI, Ł ódź (PL)

(72) Inventors: Ida Franiak-Pietryga, San Diego, CA (US); Maria Bryszewska, Ł ódź (PL); Dietmar Appelhans, Dresden (DE); Barbara Klajnert-Maculewicz, Ł ódź (PL)

(73) Assignee: UNIWERSYTET LODZKI, Lodz (PL)

( * ) Notice: Subject to any disclaimer, the term of this patent is extended or adjusted under 35 U.S.C. 154(b) by 0 days.

This patent is subject to a terminal disclaimer.

(21) Appl. No.: 15/846,143

(22) Filed: Dec. 18, 2017

(65) Prior Publication Data
US 2018/0153927 A1      Jun. 7, 2018

Related U.S. Application Data

(63) Continuation-in-part of application No. 14/650,521, filed on Jun. 8, 2015, now Pat. No. 9,877,985.

(30) Foreign Application Priority Data

Dec. 6, 2012   (PL) .......................................... 401936

(51) Int. Cl.
| A61K 31/785 | (2006.01) |
| A61K 47/59 | (2017.01) |
| C08G 83/00 | (2006.01) |
| A61P 35/02 | (2006.01) |
| A61K 9/00 | (2006.01) |
| A61K 47/26 | (2006.01) |

(52) U.S. Cl.
CPC .......... *A61K 31/785* (2013.01); *A61K 9/0024* (2013.01); *A61K 47/26* (2013.01); *A61K 47/59* (2017.08); *A61P 35/02* (2018.01); *C08G 83/003* (2013.01); *A61K 2300/00* (2013.01)

(58) Field of Classification Search
CPC .... A61K 31/785; A61K 47/59; A61K 9/0024; A61K 47/26; A61K 2300/00; A61P 35/02; C08G 83/003
See application file for complete search history.

(56) References Cited

PUBLICATIONS

Klajnert et al, The Influence of Densely Organized Maltose Shells on the Biological Properties of Poly(propylene imine) Dendrimers: New Effects Dependent on Hydrogen Bonding, 2008, Chem. Eur. J., 14, pp. 7030-7041. (Year: 2008).*

* cited by examiner

*Primary Examiner* — Trevor Love
(74) *Attorney, Agent, or Firm* — Horst M. Kasper, Esq

(57) ABSTRACT

The subject matter of the invention relates to the method of administering the polypropyleneimine dendrimer of the fourth generation, coated with maltotriose, of a general formula I, wherein 25 to 45% of R substituents stand for a maltotriose residue and each of the remaining R substituents is H, to a human subject. The dendrimer of the formula I is designated in short as PPI-G4-OS-Mal-III, where PPI-G4 stands for the 4th generation of polypropyleneimine dendrimer, OS (Open Shell)—for open coat, Mal-III for maltotriose (trisaccharide made of 3 α-glucose residues).

5 Claims, 8 Drawing Sheets

PPI-G4-OS-Mal-III dendrimer of Formula I

PPI-G4-OS-Mal-III dendrimer of Formula I

Pattern of PPI-G4-OS-Mal-III dendrimer particle
(25% substitution of primary amino groups by Mal-III with 16 R residues)

Pattern of PPI-G4-OS-Mal-III dendrimer particle
(30% substitution of primary amino groups by Mal-III with 19 R residues)

Pattern of PPI-G4-OS-Mal-III dendrimer particle
(35% substitution of primary amino groups by Mal-III with 22 R residues)

Pattern of PPI-G4-OS-Mal-III dendrimer particle
(40% substitution of primary amino groups by Mal-III with 26 R residues)

Pattern of PPI-G4-OS-Mal-III dendrimer particle
(45% substitution of primary amino groups by Mal-III with 29 R residues)

The cytometric analysis of apoptotic CLL cells under the influence of PPI-G4-OS-Mal-III dendrimer The cytomertic analysis of apoptosis in healthy lymphocytes under the influence of PPI-G4-OS-Mal-III dendrimer

APPLICATION OF MALTOTRIOSE-COATED 4TH GENERATION POLY(PROPYLENEIMINE) DENDRIMER PPI-G4-OS-MAL-III

The invention is designed for the application of maltotriose-coated 4th generation poly(propyleneimine) dendrimer PPI-G4-OS-Mal-III, wherein 25 to 45% of R substituents stand for a maltotriose residue (trisaccharide made of 3 α-glucose residues) and each of the remaining R substituents is H, which is shown in FIG. 1 and designated in short as PPI-G4-OS-Mal-III, where PPI-G4 stands for the 4th generation of poly(propyleneimine) dendrimer, OS (Open Shell) for an opencoat and Mal-III for maltotriose.

For a long time extensive research has been conducted to investigate into new effective drugs to treat hematomalignancies. For many years, standard treatment of chronic lymphocytic leukemia (CLL) was based on the application of alkylating drugs such as nitrogen mustard cyclophosphamide or chlorambucyl being a drug of choice. In the 1980s, first compounds belonging to the so-called group of purine analogues (ANP) were synthesized. Two of them, i.e. eladribine (2-chiordeoxyadenosin, 2-CdA) and fludarabine (FA) are routinely used in CLL therapy, as well as in other myelo- and lymphoproliferative disorders. Recently, a few monoclonal antibodies and immunotoxins have been introduced into CLL treatment. Monoclonal antibodies, e.g. rituximab, administered in combination with ANP, increase the effectiveness of CLL therapy.

Despite all this wide range of antileukemic drugs, CLL is still an incurable disease. Therefore, an investigation into new therapeutics, which might fight off the disease, has a deep sense, and a breakthrough in effectiveness of its treatment is much expected.

In neoplastic diseases a proliferation mechanism, i.e. the organism's ability to proliferate cells, is, in case of neoplastic cells, unlimited and uncontrolled proliferation of injured cells, which results in the occurrence of neoplastic processes in the organism. In particular, leukemic lymphocytes are regarded as showing an intensified mechanism of proliferation resulting in the occurrence of an increased number of lymphocytes in the organism in relatively short time, which leads to accumulation of hamrful B-lymphocytes in blood circulation (lymphocytosis) and a fast development of the neoplastic disease. A generally known fact (paradigm) in case of chronic lymphocytic leukemia (CLL) is the occurrence of a defect (injury) of the natural process of a programmed death of cells, i.e. apoptosis of leukemic lymphocytes present in a human organism.

An intensified worldwide development of neoplastic diseases makes us investigate into a new effective drug or drug component eliminating neoplastic diseases, including a chronic lymphocytic leukemia (CLL), a disease that is very dangerous to humans. Therefore, there is an urgent need to do research and investigate into a drug component/drug against CLL showing an ability to induce apoptosis in leukemic lymphocytes, inhibiting their proliferation (unlimited proliferation) and showing no toxicity towards other healthy blood cells at the same time.

In the 21st century, nanotechnology has been a field of studies developing rapidly. Therefore, investigations into substances that might be effective in the fight against neoplasm have been conducted in this particular area. Biologically applied nanoparticles, which have become known recently, are chemical polymeric compounds with a branched structure given the name of dendrimers. These are used as carriers of anticancer drugs through conjugation or encapsulation.

In the publication of Omidi Y, Hollins A. I, Drayton RM. Akhtar S. J Drug Target (2005), 13: 43 1-443 polypropyleneimine dendrimers (PPI) of the second and third generation used for gene (DNA fragments of a known sequence) transfection (introduction into the cell) in oncogenic lines (causing lung and skin neoplasm) were revealed. Genes introduced into neoplastic cells subject to research changed endogenous gene expression (pre-existent in the cell), also in apoptosis-related genes. It had a very advantageous impact on therapeutic results (gene therapy) resulting in death of oncogenic cells. It has been also observed that PPI vector introduced in the neoplastic cell activated genes inducing a mechanism of apoptosis.

In the publication of M Mkandawire, A Pohl, T Gubarevich, V Lapina, D Appelhans, G Rodel, W Pompe, J Schreiber, J Opitz. Selective targeting of green fluorescent nanodiamond conjugates to mitochondria in HeLa cells. J Biophotonics. 2009;2:596-606, the use of PPI-G4 dendrimers with their surface being partially maltotriose-modified (PPI-G4-OS-Mal-III) has been described in biomedical studies as carriers indicating great effectiveness in transfection of fluorescent biomarkers (nanadiamonds) towards HeLa cells.

In the studies of drugs application at particular disease stages an important criterion determining whether they are administered or not is their toxicity level for human cells. PPI-G4 poly(propyleneimine) dendrimers show very high toxicity. Thus, attempts are made to synthesize dendrimers of low toxicity as being useful in both biomedical studies and medical therapies.

Taking into account future development and availability of nanoparticles such as dendrimers, the Authors of this invention conducted extensive research with an intention to invent compounds of small molecular mass, which are capable of acting by inducing a mechanism of apoptosis in leukemic cells and showing, at the same time, low toxicity to other morphotic elements of blood.

The subject matter of the invention relates to the method of administeringthe poly(propyleneimine) dendrimer of the fourth generation, coated with maltotriose, of a general formula I, wherein 25 to 45% of R substituents stand for a maltotriose residue (trisaccharide made of 3 α-glucose residues) and each of the remaining R substituents is H, to a human subject.The dendrimer of the formula I is designated in short as PPI-G4-OS-Mal-III, where PPI-G4 stands for the 4th generation of poly(propyleneimine) dendrimer, OS (OpenShell)—for open coat, Mal-III for maltotriose.

The method comprises the steps of:
a) preparing said maltotriose-coated $4^{th}$ generation poly(propyleneimine) dendrimer—PPI-G4-OS-Mal-III of the general formula I, wherein R has the above defined meaning, in form suitable for i.v. administration, comprising a vehicle or diluent and optionally other suitable biologically active, substances, and b) administering intravenously said maltotriose-coated $4^{th}$ generation poly(propyleneimine) dendrimer—PPI-G4-OS-Mal-III of the general formula I, wherein R has the above defined meaning.

Preferably, m the general formula I, 35% of R substituents stand for a maltotriose residue and each of the remaining R substituents is H.

The method according to the invention is designed for treating or alleviating a blood neoplastic proliferative diseases with an impaired mechanism of apoptosis of a human in need thereof, said method consisting of i.v. administration of a therapeutically effective amount of the maltotriose-coated 4$^{th}$ generation poly(propyleneimine) dendrimer—PPI-G4-OS-Mal-III of the general formula I, wherein R has the meaning defined above, wherein said maltotriose-coated 4$^{th}$ generation poly(propylemeimine) dendrimer PPI-G4-OS-Mal-III is administered intravenously.

In the above method, the blood neoplastic proliferative disease with an impaired mechanism of apoptosis is a chronic lymphocytic leukemia in humans.

Preferably, the therapeutically effective amount of said PPI-G4-OS-Mal-III dendrimer is administered together with a physiological saline buffer, such as PBS (phosphate-buffered saline) as a pharmaceutically acceptable solvent suitable for i.v. administration.

The pharmaceutically acceptable solvent suitable for i.v. administration may further comprise other adjuvants and/or biolocically active substances.

ThePPI-G4-OS-Mal-III of a general formula I, wherein R has the above defined meaning intended for treating proliferative neoplastic diseases with an impaired mechanismofapoptosis. such as chronic lymphocytic leukemia, shows surprising effectiveness as an active substance causing apoptosis, i.e. a death of leukemic B-lymphocytes. It is by triggering an apoptosis mechanism that B leukemic lymphocytes die, and are next removed from the organism as injured leukemic cells and thus a therapy using the present PPI-G4-OS-Mal-III dendrimer gives positive effect.

This invention shall be described below in more details with reference to the accompanying drawings, in which.

Figure 7:
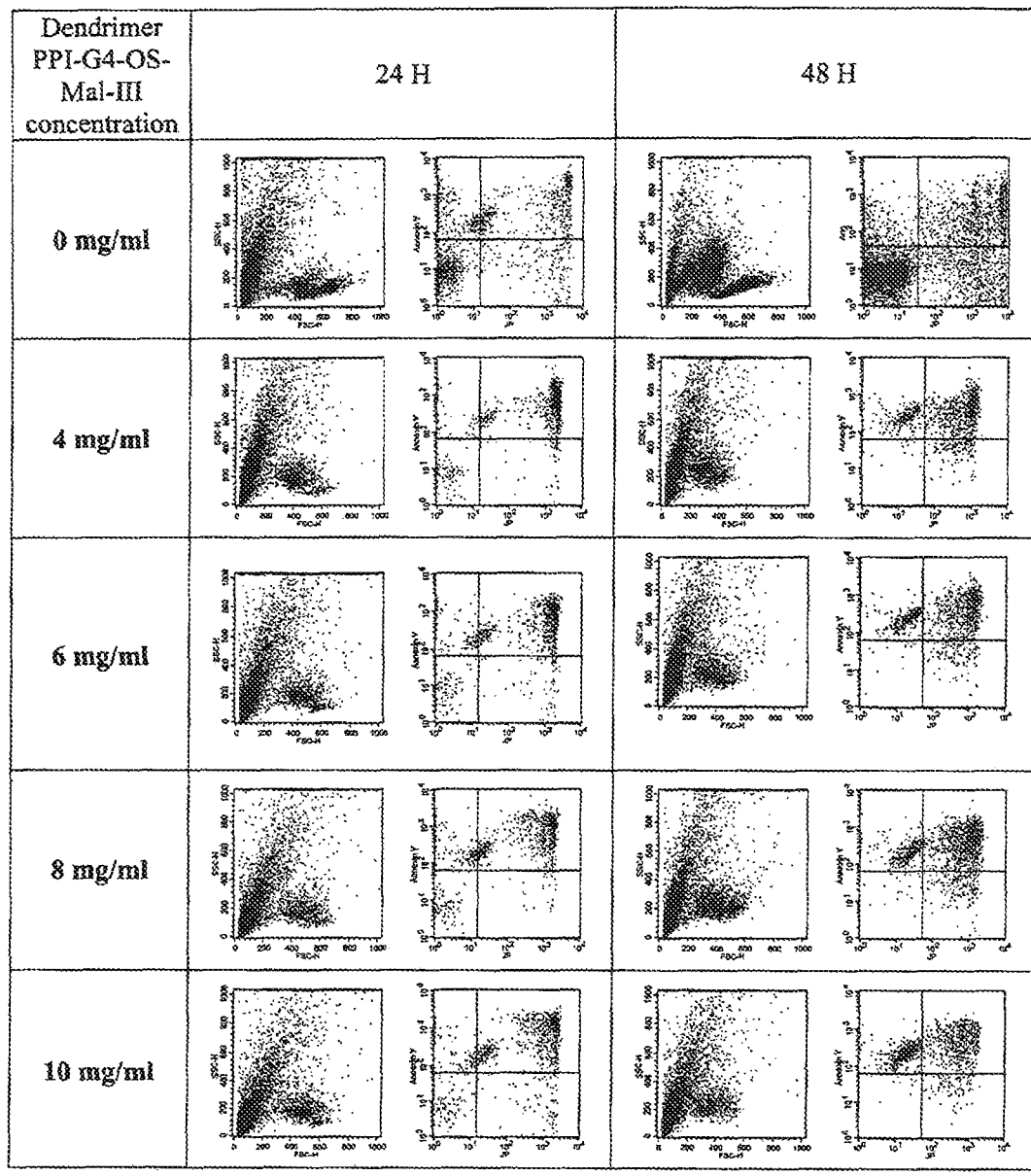
Figure 8:
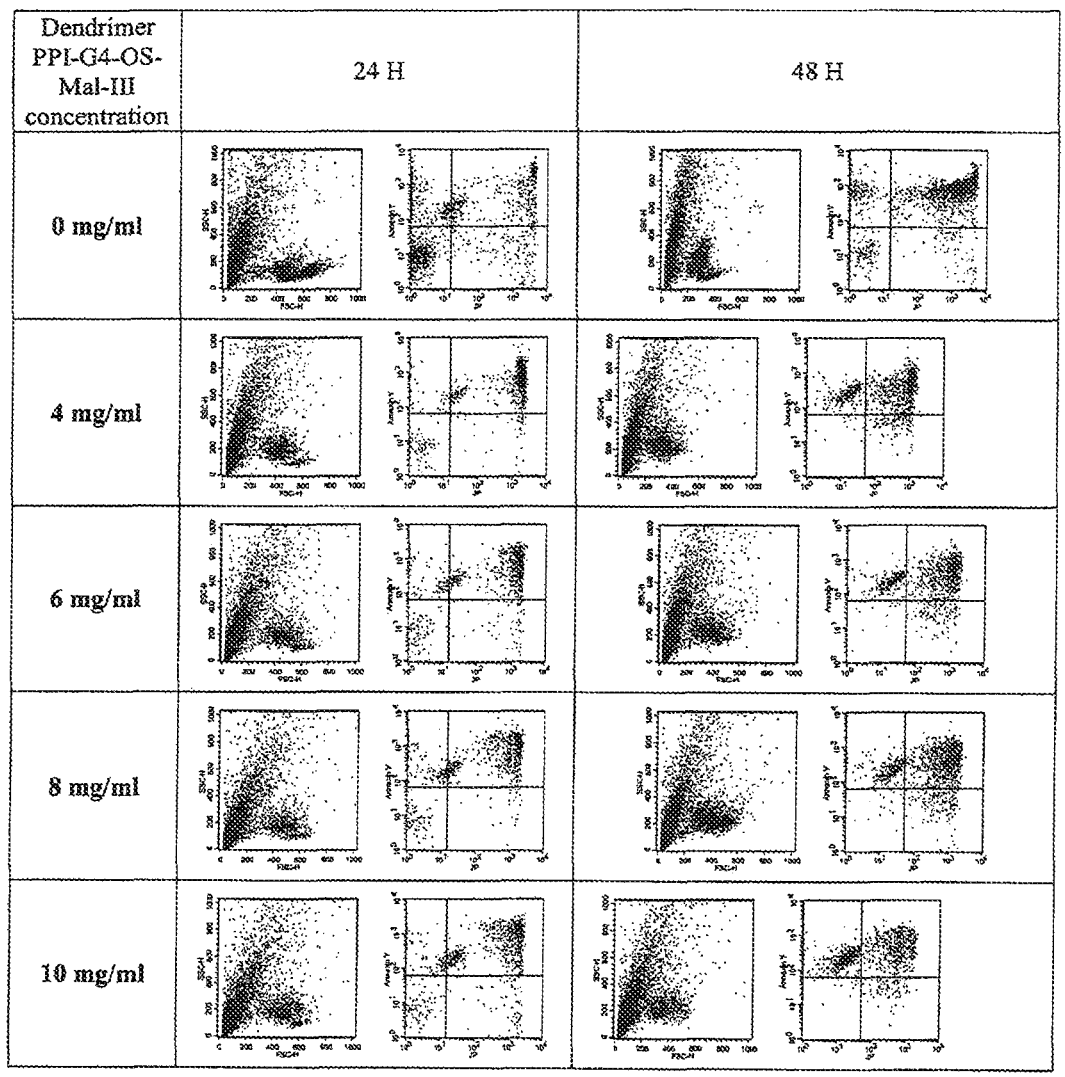

FIG. 7 presents an exemplary two-variant 'dot-plot' type histogram of control leukemic B-lymphocytes, which were not treated with the dendrimer, and leukemic B lymphocytes, which were treated with PPI-G4-OS-Mal-III dendrimer with 22 surface maltotriose residues and tested. In the doublestaining method applied (propidium iodide and annexin-V) to leukemic lymphocytes in CLL, one may observe cells being at various stages of programmed cell death (early apoptosis, late apoptosis, necrosis);

FIG. 8 presents an exemplary two-variant 'dot-plot' type histogram of healthy control B lymphocytes, which were not treated with the dendrimer, and healthy B lymphocytes, which were treated with PPI-G4-OS-Mal-III dendrimer with 22 surface maltotriose residues and tested. In the double staining method applied (propidium iodide and annexin-V) to leukemic lymphocytes in CLL, one may observe cells being at various stages of programmed cell death (early apoptosis, late apoptosis, necrosis).

The PPI-G4-OS-Mal-III dendrimer of a general formula wherein R has the above-defined meaning was found to show no toxicity in relation to morphotic elements of blood, other than leukemic B-lymphocytes. It reveals more effective biodistribution in blood.

The PPI-G4-OS-Mal-III poly(propyleneimine) dendrimer of the fourth generation, coated with maltotriose, which has been used in the methods according to the invention, and which contains maltotriose particles (Mal-III) in the dendrimer outer structure, was revealed in the publication by Appelhans D, Oertel U, Mazzeo R et al, Proc R Soc A 2010; 466; 1489-1513, containing a description of its synthesis and properties, while in the Chem. Fur J (2008), 14: 7030-7041 Klajnert B, Appelhans D, Komber H et al. described PPI-G4-OS-Mal-III dendrimer molar mass (MM) deteiuiined by magnetic resonance with use of $^1$HNMR spectrometric method, where the reading for atoms of hydrogen ($^1$H) was made at 500.13 MHz frequency.

In the accompanying drawing FIG. 2-6, the surface amino groups of PPI-G4 dendrimer are substituted with maltotriose residues (Mal-III) in 25%, 30%, 35%, 40% and 45%, respectively, to form an open dendrimer coat designated as OS (OS standing for an open shell). Coating of dendrimers with maltotriose is conducted in Germany, in Leibnitz Institute of Polymer Research, Dresden. The product is not commercially available. However, the 4$^{th}$ generation PPI dendrimers (PPI-G4) are commercially available from Symo-Chem, Eindhoven, the Netherlands. In Table 1, a molar mass (MM) of commercially available PPI-G4and synthesized PPI-G4-OS-Mal-III are given being indicative for the number and the percentage of surface R substituents standing for the maltotriose groups attached.

TABLE 1

| Dendrimer | MM$_{theoretical}$ (g/mol) | MM$_{observed}$ (g/mol) | Number (percentage) of surface Mal-III groups$_{theoretical}$ | Number (percentage) of surface Mal-III groups$_{observed}$ |
|---|---|---|---|---|
| PPI-G4 | 3514 | 3514 | — | — |
| PPI-G4-DS-Mal-III | 19144 | 14260 | 32 (50%) | 22 (35%) |

Figure 4:
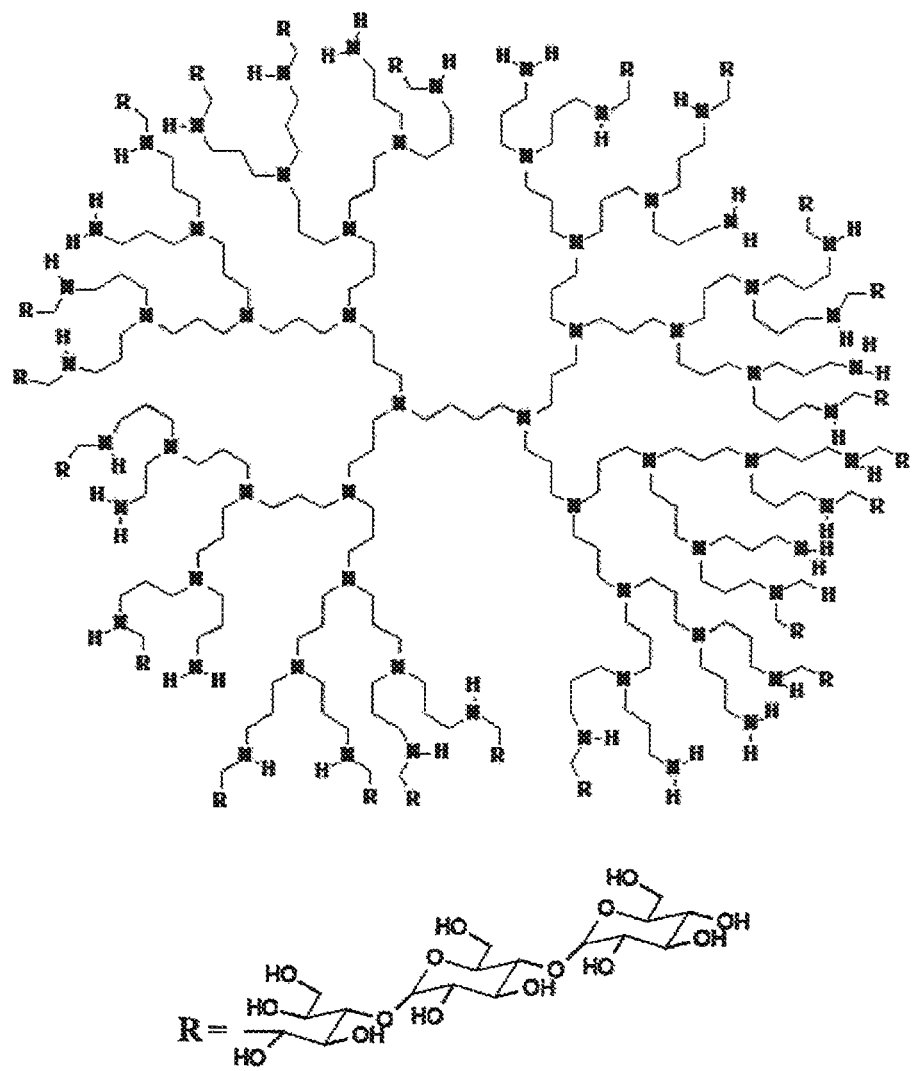
FIG. 4 shows the structure of the dendrimer of general formula I, with the 22 surface maltotriose residues.
Figure 5:
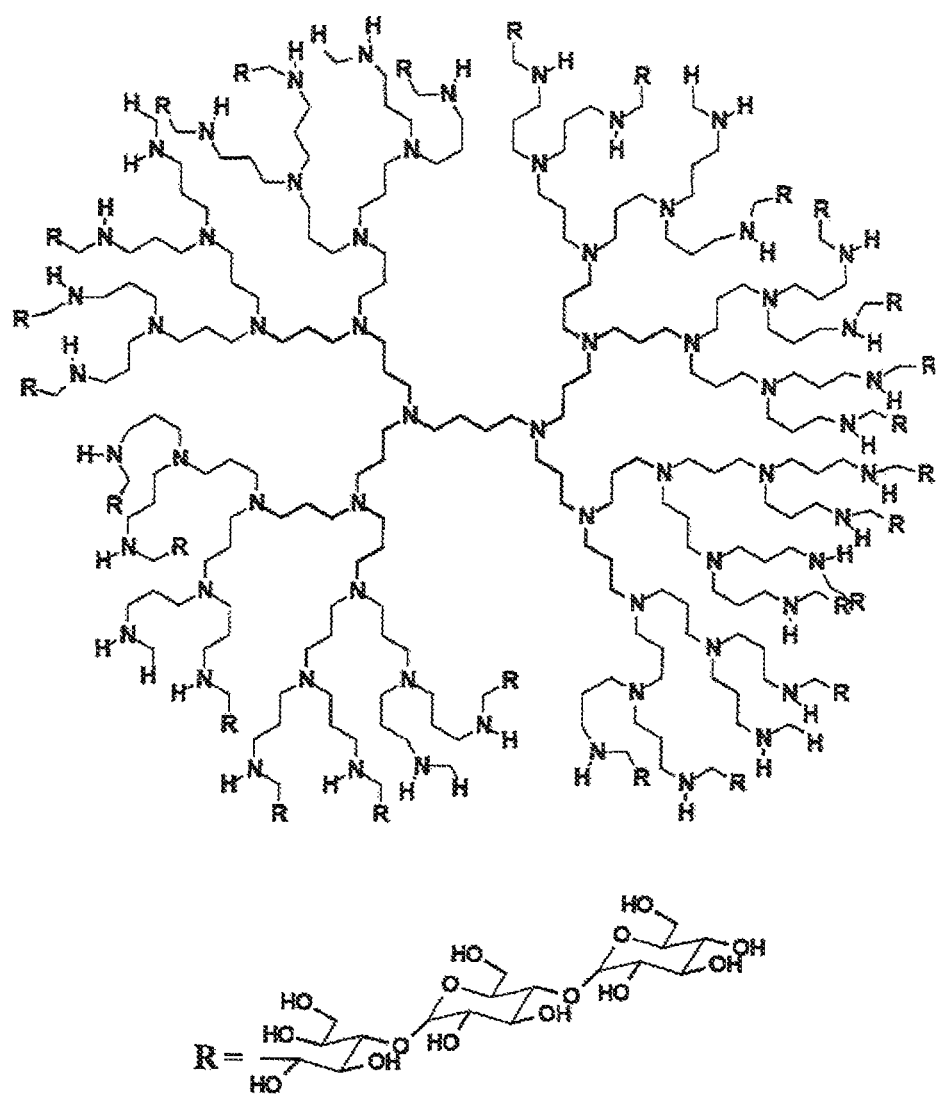
FIG. 5 shows the structure of the dendrimer of general formula I, with the 26 surface maltotriose residues.
Figure 6:
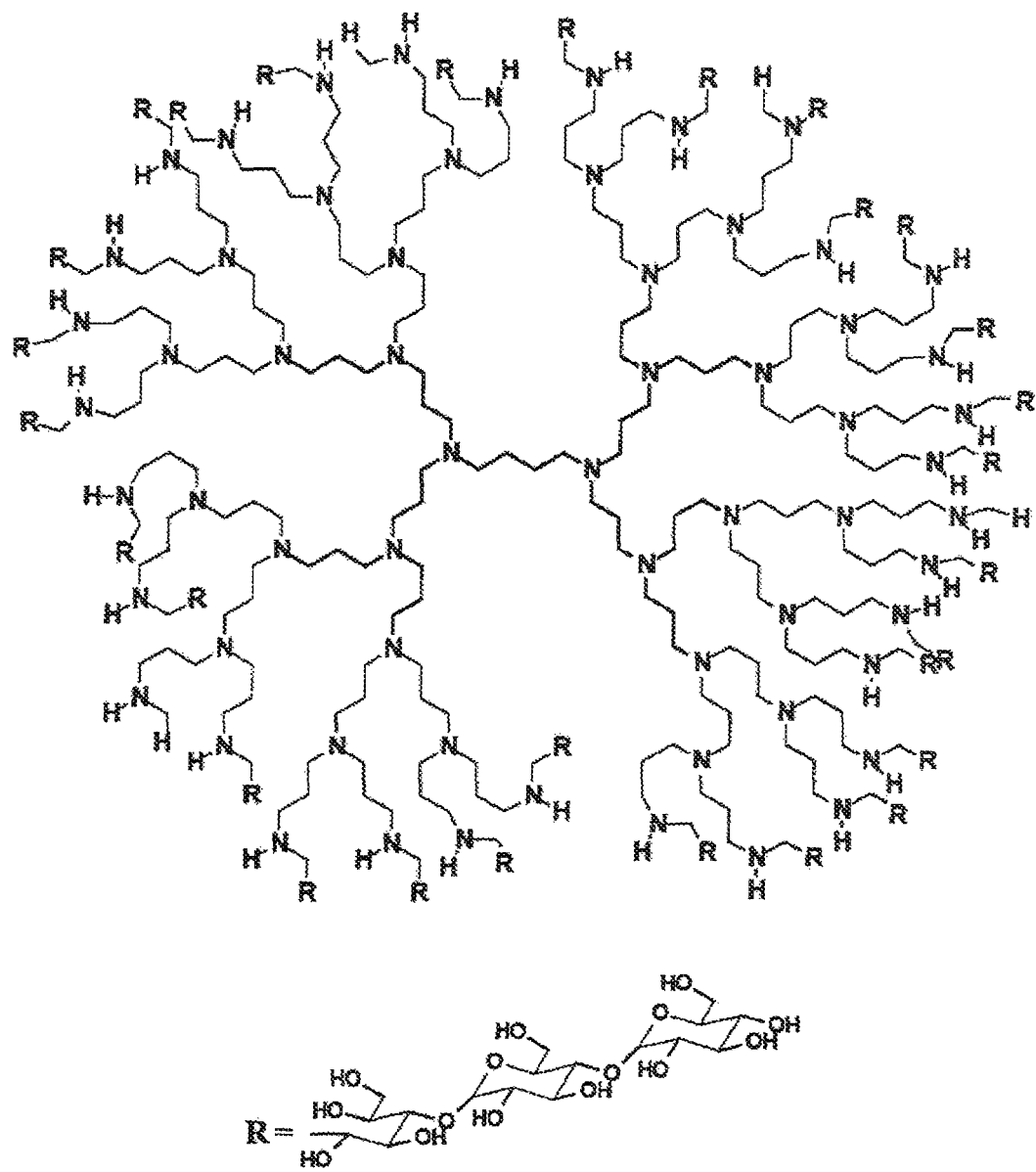
FIG. 6 shows the structure of the dendrimer of general formula I, with the 29 surface maltotriose residues.

PPI-G4-OS-Mal-III dendrimer characterized in Table 1 and shown in FIG. 4, used in the method according to the present invention was subject to tests of the IC$_{50}$, a toxicity indicator, which was defined as the concentration of dendrimers that caused 50% cytotoxicity of MNCs. The IC$_{50}$ for the PPI-G4-OS-Mal-III dendrimer used alone was 8.24 mg/ml in 48-hour cultures. Calculation of the IC$_{50}$ allows to adjust the dose of PPI-G4-OS-Mal-III dendrimer in the drug for the needs of antineoplastic therapy in treating proliferative neoplastic disorders with a disturbed apoptosis mechanism, which is the case in chronic lymphocytic leukemia, and to manufacture a composition suitable for i.v. administration in various pharmaceutical forms according to generally known methods. Similar effects were observed for dendrimers shown in FIGS. 2-3 and 5-6.

Example 1

An ability to induce the apoptosis process in leukemic lymphocytes using 4th generation polypropyleneimine dendrimer coated with maltotriose PPI-G4-OS-Mal-III of the general formula I, in which 35% R substituents stand for maltotriose residues and the remaining R substituents are H, and cytotoxicity of this dendrimer in the foregoing cells were studied—in vitro studies.

Isolation and Culture of MNCs Mononuclear Cells (Leukemic Lymphocytes) In Vitro

The research material was peripheral blood collected from 15 patients, who had not been earlier treated for chronic lymphocytic leukemia (CLL) (8 women (K) and 7 men (M) at the age of 39-85(mean age was 63.8), and who were registered as patients of the Hematology Outpatient Clinic and Hematology Department, Medical University, Łódź, Poland. The Ethics Committee of the Medical University of Łódź, Pol and approved the study (RNN/75/10/KE). Informed consent was obtained from all patients involved in the study.

Mononuclear cells (MNCs), of which a majority (approx. 90%) were B leukemic lymphocytes, were isolated from peripheral blood collected onto disodium versenate—EDTA as an anticoagulant. Next, blood was layered onto Histopaque 1077 (Sigma, St. Louis, USA) in the test tube and centrifuged on a density gradient for 20 minutes at 200 g acceleration (where 'g' means gravity acceleration). A ring of MNCs obtained at the phase boundary was isolated and washed twice with RPMI-1640 medium (PAA, Germany). MNCs obtained were suspended in RPMI-1640 medium at the concentration of $1 \times 10^6$ cells/ml; the following was subsequently added: 20% of inactivated foetal bovine serum (PBS) and antibiotics such as streptomycin, gentamicin (5 ml mixture of antibiotics per 500 ml culture medium), (PAA, Germany) and PPI-G4-OS-Mal-III dendrimer containing 35% of maltotriose in a given concentration tested (concentrations are listed below). The cultures were made in the final volume of 1 ml in the RPMI-1640 medium. The culture of MNCs was incubated in a biological incubator for 24 hours with an inflow of 5% $CO_2$ at 37° C., 98% humidity. Following the incubation process, a qualitative and quantitative assessment of MNCs apoptosis and cytotoxicity was carried out.

Using the foregoing assay, cultures of lymphocytes MNCs were made to perform tests with PPI-G4-OS-Mal-III dendrimer containing 35% in the following volumes:

4 mg/ml of culture medium,
6 mg/ml of culture medium,
8 mg/ml of culture medium,
10 mg/ml of culture medium.

In addition, tests for cultures of lymphocyte MNCs were made for 48-hours-incubation time.

The cultures made in the same conditions without PPI-G4-OS-Mal-III dendrimer containing 35% of maltotriose were considered as controls.

b) Assessment of Apoptosis and Cytotoxicity—Annexin-V and Propidium Iodide Tests Following incubation, MNCs leukemic lymphocytes were washed twice in cool buffered saline solution (PBS—saline water solution containing sodium chlorine and sodium phosphate), and next the cells were suspended in a binding buffer containing 5 μl FITC (fluorescein isothiocyanate dye) conjugated with annexin-V (Ann-V) and 10 μg/ml of propidium iodide (IP). The samples were next incubated for 15 minutes in darkness at room temperature, and their fluorescence was immediately assessed using a flow cytometer (FACSCalibur Becton Dickinson), wavelength being FL1 490"±20 nm and FL3 530"±20 nm.

Propidium iodide (IP) is a cationic solution showing autofluorescence, which is actively eliminated by healthy cells, while the cell membrane integrity is maintained (LP cells—negative, IP−). Annexin-V changes the cell membrane integrity causing a displacement of phosphatidylserine to the cell membrane outer monolayer. Cytotoxicity of the compound is demonstrated through disorders of IP release to the environment (IP—positive cells, IP+).

In order to calculate an apoptic index (AI) the cells stained with Annexin-V (AnnV+IP− and AnnV+/IP+) were assessed. Cytotoxicity of PPI-G4-OS-Mal-III containing 35% of maltotriose dendrimers was estimated by measuring viability of leukemic lymphocytes MNCs stained with IP.

Assessment of Mitochondrial Membrane Potential (Early Marker of Apoptosis)

Mitochondrial membrane potential is an early indicator of apoptosis. CMXRos, i.e. Chloromethyl-X-rosamine (the reagent's name by Mito Tracker Red CMXRos, Molecular Probes, USA), and a monoclonal antibody to glycophorin A conjugated with FITC (the reagent's name of Anti-Glycophorin A FITC by Dako, Denmark) were used for its assessment. CMXRos is a lipophilic cationic dye that accumulates in the mitochondrial matrix of viable cells when there is an electronegative load on the inner surface of the mitochondrial membrane. This asymmetric location of protons along the inner mitochondrial membrane leads to a high mitochondrial membrane potential ($\Delta\Psi m$) in living cells. A decreased $\Delta\Psi m$ is one of the first symptoms of apoptosis, and in effect lowering of the mitochondrial uptake of CMXRos.

The stock CMXRos solution was prepared by dilution of the substance supplied by the manufacturer in 94 μl. DMSO (dimethylsulphoxide), and stored at 20° C. Then working solution was prepared also using DMSO (1:10) and stored at 4° C. Mononuclear cells, i.e. leukemic lymphocytes, at $1 \times 10^6$ MNCs/ml concentration, were incubated with CMXRos (2.5 μl working solution in 500 μl RPMI 1640 medium) at 37° C. for 30 minutes. Exactly after 15 minutes, 5 μl monoclonal antibody against glycophorin A conjugated with FITC was added to eliminate any incidental erythrocytes in the sample, which might give a wrong positive result due to low mitochondrial potential. The samples were next measured using flow cytometry. The percentage of cells not bound to anti-glycophorin A-FITC ($\Delta\Psi m^{low}/Gly\text{-}A^-$ cells), with low mitochondrial potential, was calculated.

All fluorescence measurements were performed by a flow cytometer FACSCalibur (Becton Dickinson, USA) equipped with an argon laser 488nm and computer program CeliQuestPro (Becton Dickinson, USA). Each time 10 000cells were evaluated. The fluorescence was measured using standard emission filters: green—FL1 (wavelength $\lambda=530\pm20$ nm) and red—FL3 ($\lambda>600$ nm).

Statistical Analysis

Significant statistical differences between the results obtained in cultures of leukemic lymphocytes (MNCs), where PPI-G4-OS-Mal-III dendrimer containing 35% of maltotriose was added as in the invention and control cultures, where no such PPI-G4-OS-Mal-III dendrimer was added, were compared using Wilcoxon rank test and assuming that statistically significant differences were those in which a significance level was p<0.05.

The $IC_{50}$ toxicity indicator of PPI-G4-OS-Mal-III dendrimer was defined as the concentration of dendrimers that caused 50% cytotoxicity of leukemic lymphocytes (MNCs). Calculation of the $IC_{50}$ allows adjusting the dose of the drug containing PPI-G4-OS-Mal-III dendrimer for the needs of antineoplastic therapy. If it is necessary for a single dose of the drug to be so toxic as to destroy 100% cells against which it is directed, then in such a drug dose the PPI-G4-OS-Mal-III dendrinder concentration is twice as high as the concentration causing death of 50% of leukemic cells. This applies to drug doses for patients with progressive disease in whom a fast therapeutic effect would be recommended (fewer tablets given in short time). In case of weaker patients, e.g. elderly patients, a dose of the drug containing PPI-G4-OS-Mal-III dendrimer shall be established at the concentration reduced by half to destroy leukemic lymphocytes. The therapy shall take more time, and there will be fewer adverse effects as a response to the cell disintegration process; however, the final therapeutic effect shall be achieved (more tablets taken in longer time by the patient, therapeutic effect achieved).

Results Obtained

The percentage of apoptotic MNCs induced by PPI-G4-OS-Mal-III dendrimer in each concentration after 24 h and 48 h incubations was significantly higher than the percentage of spontaneous apoptotic leukemic cells (p<0.05) (Table 2). Cytometric analysis of CLL cells undergoing apoptosis is shown in FIG. 7. A higher percentage of cells undergoing apoptosis was observed for 48 h incubation time, compared to 24 h. The greatest differences for late apoptotic cells (Ann-V$^+$IP$^+$) were shown after 48h incubation at two dendrimer concentration of 8 mg/ml (p=0.007) and 10 mg/ml (p=0.007), however, after 24 h incubation the difference from controls was also significant (p=0.005)—see Table 2, which presents results of mean percentage of leukemic lymphocytes in in vitro cultures subject to apoptosis or necrosis under the influence of PPI-G4-OS-Mal-III dendrimer in four concentrations examined; in addition, the results provide for the values of standard deviation in relation to each mean value and statistical analysis).

PPI-G4-OS-Mal-III dendrimer did not markedly induced an early apoptosis (Ann-V$^+$IP$^-$) of CLL cells. No statistically significant differences were observed for the percentage of CLL necrotic cells as compared to control cultures either in 24 h-cultures or in 48 h-cultures. This indicates that the tested dendrimer PPI-G4-OS-Mal-III causes CLL cells' death by inducing the apoptosis mechanism and does not act directly on the cell membrane by interrupting its integrity. IC$_{50}$ for PPI-G4-OS-Mal-III dendrimer used alone was 8.24mg/ml.

Another method confirming the activity of PPI-G4-OS-Mal-III dendrimer via the mechanism of apoptosis on CLL cells is the evaluation of mitochondrial potential. In 24-hour cultures with dendrimer in three concentrations, i.e. 4 mg/ml, 6 mg/ml, 8 mg/ml, the number of apoptotic cells was significantly higher than the number of cells in the control culture. The percentage of apoptotic cells increased proportionally with increasing concentrations of the dendrimer. The apoptotic cells rate after the incubation with the purine analogue (FA, fludarabine) at the concentration of 1.6 µM was comparable to the percentage of apoptotic cells for the PPI-G4-OS-Mal-III dendrimer concentration of 6 mg/ml. Monoclonal antibody anty-CD20 (Rit, rituximab) at the concentration of 10 µg/ml showed apoptosis-inducing action in order of spontaneous apoptosis (in control samples). After 48 h in cell cultures with the dendrimer, the percentage of cells ΔΨm$^{low}$/GIy-A$^-$ was significantly higher (68.57-78.56%) than the percentage of cells in the control culture (42.04%). The results are shown in Table 4, which presents results of averaged percentage of cells—leukemic lymphocytes with a decreased mitochondrial potential in in vitro cultures under the influence of PPI-G4-OS-Mal-III dendrimer in three concentrations examined and under the influence of two drugs most frequently used in CLL therapy, i.e. fludarabine (purine analogue) and rituximab (monoclonal antibody).

Example 2

An ability to induce the apoptosis process in healthy blood cells using 4th generation polypropyleneimine dendrimer coated with maltotriose PPI-G4-Mal-III containing 35% of maltotriose, and cytotoxicity of this dendrimer in the foregoing cells were studied—in vitro studies.

Assessment of the Apoptosis Induction and PPI-G4-OS-Mal-III Dendrimer's Cytotoxicity in MNCs from Healthy Vvolunteers The research material was peripheral blood collected from 5 healthy volunteers, (3 women and 2 men) at the age of 25-65 (mean age was 38,00±10,80). Isolation of mononuclear cells (MNCs), cell cultures, also assessment of apoptosis and cytotoxicity were made using the same method as in Example 1 .

The effect of PPI-G4-OS-Mal-III dendrimer on healthy mononuclear cells is negligible; however, differences between control cultures and cultures with dendrimer show statistical significance. It is only after 48 h that higher percentage of apoptotic cells was observed for higher dendrimer concentrations. Statistically significant results were obtained for late apoptosis at every examined dendrimer PPI-G4-OS-Mal-III concentration (p=0.03). The percentage of dead cells IP stained after 24 h incubation was equal to 23.33% for PPI-G4-OS-Mal-III dendrimer concentration of 8 mg/ml, whereas it was 12.38% for the dendrimer untreated cells. As demonstrated by the presented results, PPI-G4-OS-Mal-III dendrimer show not much toxicity to healthy lymphocytes (FIG. 8) and Table 3, which presents results of mean percentage of healthy lymphocytes in in vitro cultures subject to apoptosis or necrosis under the influence of PPI-G4-OS-Mal-III dendrimer in four concentrations examined; in addition, the results provide for the values of standard deviation in relation to each mean value and statistical analysis.

Influence of PP-G4-DS-Mal-III Dendrimer on Inhibition or Induction of MNCs Lymphocytes Proliferation MNCs were isolated using the method of density gradient (as described in Example 1) from the blood of healthy volunteers. To assess the inhibition or induction of lymphocyte proliferation by PPI-G4-OS-Mal-III dendrimer, cells were incubated with or without the dendrimer, and either in the presence or absence of phytohemaglutinin (PHA-M) depending on whether it was a tested sample or a control one respectively. After 72 h incubation, the samples were analysed spectrophotornetrically by means of MTT (3-(-4,5-dimethyl-2-thiazolyl)-2,5-diphenyl- 2H-tetrazolium bromide). The final concentration of PHA-M was 10 µl/ml 10 ml and PPI-G4-OS-Mal-III dendrimers were used at concentrations of 0.2, 0.04 and 0.008 mg/ml. The MNCs suspension with PHA-M solution at 10 µl/ml concentration in the culture medium was regarded as a positive-proliferating control, and the MNCs suspension in the PBS buffer was regarded as the negative-nonproliferating control.

The PPI-G4-OS-Mal-III dendrimer slightly restrained cell proliferation of healthy lymphocytes. This effect is of no considerable significance from the biological point of view. The ability to inhibit proliferation increases proportionally with increasing concentration of the dendrimer PPi-G4-OS-Mal-III.

Influence of PPI-G4-DS-Mal-III Dendrimers on Erythrocyte Haemolysis

In the samples subject to tests the level of haemolysis was determined on the basis of haemoglobin (HGB) released into the supernatant during centrifuging of 1000 g for 5 minutes, and after prior incubation at 37° C. for 2, 4, 16and 24 h. For reference (100% haemolysis), erythrocytes were treated with distilled water. The PPI-G4-OS-Mal-III dendrimers did not cause erythrocyte haemolysis in contrast to unmodified dendrimers (PPI-G4). It is obvious from the above observation that PPI-G4-OS-Mal-III dendrimer containing 35% of maltotriose is safe for erythrocytes; it does not destroy their cell membranes.

Influence of PPI-G4-OS-Mal-III Dendrimers on Platelets (PLT) Aggregation

Blood from healthy donors was collected onto LPDA-1 anticoagulant (100 mM glucose; 55 mM mannitol; 25.8 mM $K_2PO_4$; 14.7 mM $KH_2PO_4$; 17.9 mM potassium citrate); (mM—molar mass). Blood plasma was centrifuged at 360 g (g—gravity acceleration) for 5 minutes. PLTs pellet (a cluster of cells following centrifuging devoid of supernatant) was suspended in Tris (TRIS—tris(hydroxymethy)aminomethane buffer containing EDTA (0.12 M NaCl, 0.0154 M KCl, 0.006 glucose, 0.0015 M $Na_2EDTA$, 0.0133 M Tris; pH 6.5) (M—Mol). The suspension was centrifuged at 360 g for 5 minutes. The pellet was re-suspended in the buffer at concentration of $2.0 \times 10^9$ cells/ml (TRIS buffer). Aggregation of PLTs was determined using an automatic agregometer AP2110. Trypsin at concentration of 1 μg/ml was added to PLTs as a positive control.

The PPI-G4-OS-Mal-III dendrimer caused the PLT aggregation in 20% at the concentration of 10 mg/ml and higher.

As described above, PPI-G4-OS-Mal-III dendrimer supplementation to CLL lymphocytes significantly induces the mechanism of apoptosis in these cells, thus considerably reducing their proliferation and survival. It has been proved that one may expect an effective therapeutic effect in treating proliferative neoplastic diseases, particularly chronic lymphocytic leukemia (CLL), using the PPI-G4-OS-Mal-III dendrimer as a drug. At the same time, it has been proved that the PPT-G4-OS-Mal-III dendrimer applied in the way presented in the invention, is non-toxic to other morphotic elements of blood (erythrocytes, platelets), which ensures its safe use in humans.

TABLE 2

The influence of the PPI-G4-OS-Mal-III dendrimer on apoptosis and viability of CLL cells in in vitro cultures.

| | Control | | | PPI-G4-OS-Mal-III 4 mg/ml | | | PPI-G4-OS-Mal-III 6 mg/ml | | | PPI-G4-OS-Mal-III 8 mg/ml | | | PPI-G4-OS-Mal-III 10 mg/ml | | | Statistical analysis (P) 13 |
|---|---|---|---|---|---|---|---|---|---|---|---|---|---|---|---|---|
| | 1 Ann+ IP− | 2 Ann+ IP+ | 3 Ann− IP+ | 4 Ann+ IP− | 5 Ann+ IP+ | 6 Ann− IP+ | 7 Ann+ IP− | 8 Ann+ IP+ | 9 Ann− IP+ | 10 Ann+ IP− | 11 Ann+ IP+ | 12 Ann− IP+ | 13 Ann+ IP− | 14 Ann+ IP+ | 15 Ann− IP+ | |
| | | | | | | | 24 h | | | | | | | | | |
| n | 15 | 15 | 15 | 15 | 15 | 15 | 15 | 15 | 15 | 15 | 15 | 15 | 15 | 15 | 15 | 2 v 5 = 0.005 |
| X | 9.46 | 7.57 | 4.25 | 11.84 | 22.41 | 6.94 | 14.46 | 22.79 | 5.82 | 14.95 | 24.43 | 5.37 | 21.14 | 25.43 | 10.34 | 2 v 8 = 0.005 |
| SD | 9.83 | 6.72 | 2.63 | 8.02 | 20.22 | 8.52 | 12.31 | 17.68 | 5.47 | 12.71 | 18.14 | 5.58 | 22.14 | 26.93 | 5.23 | 2 v 11 = 0.005 |
| | | | | | | | | | | | | | | | | 2 v 14 = 0.005 |
| | | | | | | | 48 h | | | | | | | | | |
| n | 15 | 15 | 15 | 15 | 15 | 15 | 15 | 15 | 15 | 15 | 15 | 15 | 15 | 15 | 15 | 2 v 5 = 0.05 |
| X | 11.70 | 15.30 | 11.95 | 11.41 | 28.86 | 8.80 | 10.23 | 31.07 | 8.61 | 10.25 | 34.76 | 12.46 | 15.47 | 45.66 | 15.02 | 2 v 8 = 0.01 |
| SD | 8.75 | 11.77 | 13.61 | 9.84 | 20.42 | 5.52 | 7.91 | 21.78 | 6.09 | 7.80 | 21.78 | 12.90 | 13.96 | 3.92 | 7.85 | 2 v 11 = 0.007 |
| | | | | | | | | | | | | | | | | 2 v 14 = 0.007 | n—number of samples; X—mean percentage of apoptotic or necrotic cells; SD—standard deviation;
Early apoptosis - Ann+IP−; late apoptosis - Ann+IP+; necrosis - Ann−IP+; Ann—annexin-V; IP—propidium iodide

TABLE 3

The influence of the PPI-G4-OS-Mal-III dendrimer on apoptosis and viability of healthy cells in in vitro cultures.

| | Control | | | PPI-G4-OS-Mal-III 4 mg/ml | | | PPI-G4-OS-Mal-III 6 mg/ml | | | PPI-G4-OS-Mal-III 8 mg/ml | | | PPI-G4-OS-Mal-III 10 mg/ml | | | Statistical analysis (P) 13 |
|---|---|---|---|---|---|---|---|---|---|---|---|---|---|---|---|---|
| | 1 Ann+ IP− | 2 Ann+ IP+ | 3 Ann− IP+ | 4 Ann+ IP− | 5 Ann+ IP+ | 6 Ann− IP+ | 7 Ann+ IP− | 8 Ann+ IP+ | 9 Ann− IP+ | 10 Ann+ IP− | 11 Ann+ IP+ | 12 Ann− IP+ | 13 Ann+ IP− | 14 Ann+ IP+ | 15 Ann− IP+ | |
| | | | | | | | 24 h | | | | | | | | | |
| n | 5 | 5 | 5 | 5 | 5 | 5 | 5 | 5 | 5 | 5 | 5 | 5 | 5 | 5 | 5 | 1 v 4 = 0.04 |
| X | 11.0 | 4.11 | 8.27 | 6.68 | 15.53 | 7.11 | 7.53 | 17.15 | 8.61 | 8.55 | 16.53 | 8.80 | 10.66 | 19.75 | 11.66 | 2 v 5 = 0.04 |
| SD | 1.97 | 0.76 | 1.22 | 1.91 | 2.46 | 1.29 | 2.39 | 3.10 | 2.40 | 2.84 | 3.23 | 1.82 | 2.35 | 1.57 | 3.13 | 2 v 8 = 0.04 |
| | | | | | | | | | | | | | | | | 2 v 11 = 0.04 |
| | | | | | | | | | | | | | | | | 2 v 14 = 0.04 |
| | | | | | | | 48 h | | | | | | | | | |
| n | 5 | 5 | 5 | 5 | 5 | 5 | 5 | 5 | 5 | 5 | 5 | 5 | 5 | 5 | 5 | 2 v 5 = 0.03 |
| X | 18.05 | 13.02 | 10.56 | 7.91 | 23.90 | 7.96 | 7.19 | 25.45 | 12.63 | 8.70 | 26.17 | 10.09 | 9.39 | 32.10 | 9.54 | 2 v 8 = 0.03 |
| SD | 4.71 | 1.22 | 3.41 | 1.49 | 5.27 | 1.43 | 1.87 | 5.42 | 3.56 | 2.26 | 6.43 | 1.54 | 3.23 | 5.79 | 1.40 | 2 v 11 = 0.03 |
| | | | | | | | | | | | | | | | | 2 v 14 = 0.03 | n—number of samples; X—mean percentage of apoptotic or necrotic cells; SD—standard deviation;
Early apoptosis - Ann+IP−; late apoptosis - Ann+IP+; necrosis - Ann−IP+; Ann—annexin-V; IP—propidium iodide

TABLE 4

The influence of the PPI-G4-OS-Mal-III dendrimer on CLL cell mitochondrial potential in cultures in vitro. The comparison with purine analogue (fludarabine; FA) and monoclonal antibody (rituximab; Rit).

|   | Control | PPI-G4-OS-Mal-III 4 mg/ml | PPI-G4-OS-Mal-III 6 mg/ml | PPI-G4-OS-Mal-III 8 mg/ml | FA 1.6 µM | Rit 10 µg/ml |
|---|---|---|---|---|---|---|
| | | | 24 h | | | |
| n | 10 | 10 | 10 | 10 | 10 | 10 |
| X | 37.91 | 49.30 | 59.88 | 63.98 | 52.05 | 44.92 |
| SD | 16.23 | 12.94 | 15.12 | 13.49 | 17.81 | 16.70 |
| | | | 48 h | | | |
| n | 10 | 10 | 10 | 10 | 10 | 10 |
| X | 42.04 | 68.57 | 70.88 | 78.56 | 74.49 | 60.58 |
| SDb | 14.26 | 18.49 | 15.45 | 11.56 | 17.47 | 19.99 | n—number of samples; X—mean percentage of cells with lower mitochondrial potential ($\Delta\Psi m^{low}$/Gly-A$^-$ [%]); SD—standard deviation; FA—fludarabine; Rit—rituximab Example 3

Following the procedures of Example 1, an ability to induce the apoptosis process in leukemic lymphocytes using 4th generation poly(propyleneimine) dendrimers coated with maltotriose PPI-G4-OS-Mal-III of the general formula I, in which 25%, 30%, 40% or 45% of the R substituents stand for maltotriose residues (the remaining Rs being H) and cytotoxicity of those dendrimers in the foregoing cells were studied—in vitro studies.

Isolation and Culture of MNCs Mononuclear Cells (Leukemic Lymphocytes) In Vitro

The research material was the same as in Example 1, i.e. the peripheral blood collected from 15 patients, who had not been earlier treated for chronic lymphocytic leukemia (CLL) (8 women (K) and 7 men (M) at the age of 39-85(mean age was 63.8), and who were registered as patients of the Hematology Outpatient Clinic and Hematology Department, Medical University, Łódź, Poland. The Ethics Committee of the Medical University of Łódź, Poland approved the study (RNN/75/10/KE). Informed consent was obtained from all patients involved in the study.

Mononuclear cells (MNCs), of which a majority (approx. 90%) were B leukemic lymphocytes, were isolated from peripheral blood collected onto disodium versenate—EDTA as an anticoagulant. Next, blood was layered onto Histopaque 1077 (Sigma, St. Louis, USA) in the test tube and centrifuged on a density gradient for 20 minutes at 200 g acceleration (where 'g'means gravity acceleration). A ring of MNCs obtained at the phase boundary was isolated and washed twice with RPM-1640 medium (PAA, Germany). MNCs obtained were suspended in RPMI-1640 medium at the concentration of $1\times10^6$ cells/ml; the following was subsequently added: 20% of inactivated fetal bovine serum (FBS) and antibiotics such as streptomycin, gentamicin (5 ml mixture of antibiotics per 500 ml culture medium), (PAA, Germany) and four different PPI-G4-OS-Mal-III dendrimers of the general formula I, in which respectively 25%, 30%, 40% or 45% R substituents stand for maltotriose residues (the remaining R substituents being H) in a given concentration tested (concentrations are listed below in corresponding Tables 5-8). The cultures were made in the final volume of 1 ml in the RPMI-1640 medium. The culture of MNCs was incubated in a biological incubator for 24 hours with an inflow of 5% $CO_2$ at 37° C., 98% humidity. Following the incubation process, a qualitative and quantitative assessment of MNCs apoptosis and cytotoxicity was carried out.

Using the foregoing assay, cultures of lymphocytes MNCs were made to perform tests with PPI-G4-OS-Mal-III dendrimers of the general formula I, in which 25%, 30%, 40% or 45% R substituents stand for maltotriose residues (the remaining R substituents being H) in the following volumes:

4 mg/ml of culture medium,
6 mg/ml of culture medium,
8 mg/ml of culture medium,
10 mg/ml of culture medium.

In addition, tests for cultures of lymphocyte MNCs were made for 48-hours-incubation time.

The cultures made in the same conditions without PPI-G4-OS-Mal-III dendrimers of the general formula I, in which 25%, 30%, 40% or 45% R substituents stand for maltotriose residues (the remaining R substituents being H) were considered as controls.

Assessment of Apoptosis and Cytotoxicity-Annexin-V and Propidium Iodide Tests

Following incubation, MNCs leukemic lymphocytes were washed twice in cool buffered saline solution (PBS—saline water solution containing sodium chlorine and sodium phosphate), and next the cells were suspended in a binding buffer containing 5 µl FITC (fluorescein isothiocyanate dye) conjugated with annexin-V (Ann-V) and 10 µg/ml of propidium iodide (IP). The samples were next incubated for 15 minutes in darkness at room temperature, and their fluorescence was immediately assessed using a flowcytometer (FACSCalibur Becton Dickinson), wavelength being FL1 490"±20 nm and FL3 530"20 mn.

Propidium iodide (IP) is a cationic solution showing autofluorescence, which is actively eliminated by healthy cells, while the cell membrane integrity is maintained (IP cells—negative, IP−). Annexin-V changes the cell membrane integrity causing adisplacement of phosphatidylserine to the cell membrane outer monolayer. Cytotoxicity of the compound is demonstrated through disorders of IP release to the environment (IP—positive cells, IP+)

In order to calculate an apoptotic index (AI) the cells stained with Annexin-V (AnnV+IP− and AnnV+/IP+) were assessed. Cytotoxicity of PPI-G4-OS-Mal-III dendrimers of the general formula I, in which 25%, 30%, 40% or 45% R substituents stand for maltotriose residues (the remaining R substituents being H) was estimated by measuring viability of leukemic lymphocytes MNCs stained with IP.

Assessment of Mitochondrial Membrane Potential (Early Marker of Apoptosis)

Mitochondrial membrane potential is an early indicator of apoptosis. CMXRos, i.e. Chloromethyl-X-rosamine (the reagent's name by Mita Tracker Red CMXRos, Molecular Probes, USA), and a monoclonal antibody to glycophorin A conjugated with FITC (the reagent's name of Anti-Glycophorin A FITC by Dako, Denmark) were used for its assessment. CMXRos is a lipophilic cationic dye that accumulates in the mitochondrial matrix of viable cells when there is an electronegative load on the inner surface of the mitochondrial membrane. This asymmetric location of protons along the inner mitochondrial membrane leads to a high mitochondrial membrane potential ($\Delta\Psi m$) in living cells. A decreased $\Delta\Psi m$ is one of the first symptoms of apoptosis, in effect lowering of the mitochondrial uptake of CMXRos.

The stock CMXRos solution was prepared by dilution of the substance supplied by the manufacturer in 94 µl DMSO (dimethylsulphoxide), and stored at 20° C. Then working solution was prepared also using DMSO (1:10) and stored at 4° C. Mononuclear cells, i.e. leukemic lymphocytes, at $1\times10^6$ MNCs/ml concentration, were incubated with CMXRos (2.5 µl working solution in 500 µl RPMI 1640 medium) at 37° C. for 30 minutes. Exactly after 15 minutes, 5 µl of monoclonal antibody against glycophorin A conjugated with FITC was added to eliminate any incidental erythrocytes in the sample, which might give a wrong positive result due to low mitochondrial potential. The samples were next measured using flow cytometry. The percentage of cells not bound to anti-glycophorin A-FITC ($\Delta\Psi m^{low}$/Gly-A$^-$ cells), with low mitochondrial potential, was calculated.

All fluorescence measurements were performed by a flow cytometer FACSCalibur (Becton Dickinson, USA) equipped with an argon laser 488nm and computer program CellQuestPro (Becton Dickinson, USA). Each time 10 000 cells were evaluated. The fluorescence was measured using standard emission filters: green—F1 (wavelength $\lambda$=530±20 nm) and red FL3 ($\lambda$>600 nm).

Statistical Analysis

Significant statistical differences between the results obtained in cultures of leukemic lymphocytes (MNCs), where PPI-G4-OS-Mal-III dendrimers of the general formula I, in which 25%, 30%, 40% or 45% R substituents stand for maltotriose residues (the remaining R substituents being H) were added as in the invention and control cultures, where no such PPI-G4-OS-Mal-III dendrimer was added, were compared using Wilcoxon rank test and assuming that statistically significant differences were those in which a significance level was p<0.05.

The IC$_{50}$ toxicity indicator of PPI-G4-OS-Mal-III dendrimer was defined as the concentration of dendrimers that caused 50% cytotoxicity of leukemic lymphocytes (MNCs). Calculation of the IC$_{50}$ allows adjusting the dose of the drug containing PPI-G4 OS-Mal-III dendrimer for the needs of antineoplastic therapy. If it is necessary for a single dose of the drug to be so toxic as to destroy 100% cells against which it is directed, then in such a drug dose the PPI-G4-OS-Mal-III dendrimer concentration is twice as high as the concentration causing death of 50% of leukemic cells. This applies to drug doses for patients with progressive disease in whom a fast therapeutic effect would be recommended (fewer tablets given in short time). In case of weaker patients, e.g. elderly patients, a dose of the drug containing PPI-G4-OS-Mal-III dendrimer shall be established at the concentration reduced by half to destroy leukemic lymphocytes. The therapy shall take more time, and there will be fewer adverse effects as a response to the cell disintegration process; however, the final therapeutic effect shall be achieved (more tablets taken in longer time by the patient, therapeutic effect achieved).

Results Obtained

The results obtained in accordance with the Examples are summarized in the Tables 5-8 below.

The percentage of apoptotic MNCs induced by PPI-G4-OS-Mal-III dendrimers in each concentration after 24 h and 48 h incubations was significantly higher than the percentage of spontaneous apoptotic leukemic cells (p<0.05). Cytometric analysis of CLL cells undergoing apoptosis is shown in FIG. 7. A higher percentage of cells undergoing apoptosis was observed for 48 h incubation time, compared to 24 h. The greatest differences for late apoptotic cells (Ann-V$^+$IP$^+$) were shown after 48 h incubation at two dendrimer concentration of 8mg/ml (p=0.007) and 10 mg/ml (p=0.007), however, after 24 h incubation the difference from controls was also significant (p=0.005).

PPI-G4-OS-Mal-III dendrimers did not markedly induce an early apoptosis (Ann-V$^+$IP$^{31}$) of CLL cells. No statistically significant differences were observed for the percentage of CLL necrotic cells as compared to control cultures either in 24 h-cultures or in 48 h-cultures. This indicates that the tested dendrimer PPI-G4-OS-Mal-III causes CLL cells' death by inducing the apoptosis mechanism and does not act directly on the cell membrane by interrupting its integrity. IC$_{50}$ for PPI-G4-OS-Mal-III dendrimer used alone was 8.24 mg/ml.

Another method confirming the activity of PPI-G4-OS-Mal-III dendrimers via the mechanism of apoptosis on CLL cells is the evaluation of mitochondrial potential. In 24-hour cultures with a dendrimer in three concentrations. i.e. 4 mg/ml, 6 mg/ml, 8 mg/ml, the number of apoptotic cells was significantly higher than the number of cells in the control culture. The percentage of apoptotic cells increased proportionally with increasing concentrations of the dendrimer. The apoptotic cells rate after the incubation with the purine analogue (FA, fludarabine) at the concentration of 1.6 µM was comparable to the percentage of apoptotic cells for the PPI-G4-OS-Mal-III dendrimer concentration of 6 mg/ml. Monoclonal antibody anty-CD20 (Rit, rituximab) at the concentration of 10 µg/ml showed apoptosis-inducing action in order of spontaneous apoptosis (in control samples). After 48 h in cell cultures with the dendrimer, the percentage of cells $\Delta\Psi$m/Gly-A$^-$ was significantly higher (68.57-78.56%) than the percentage of cells in the control culture (42.04%).

Example 4

The procedures described in Example 2 to assess in vitro the ability of the 4th generation poly(propyleneimine) dendrimer coated with maltotriose PPI-G4-OS-Mal-III containing 35% of maltotriose to induce the apoptosis process in healthy blood cells and cytotoxicity of this dendrimer in the foregoing cells, were repeated using the PPI-G4-OS-Mal-III dendrimers of the general formula I, in which 25%, 30%, 40% or 45% R substituents stand for maltotriose residues and the remaining R substituents are H, and using the same research material, i.e. the peripheral blood collected from 5 healthy volunteers, (3 women and 2 men) at the age of 25-65 (mean age was 38.00±10.80) and the same methods for the assessment of the apoptosis induction and PPI-G4-OS-Mal-III dendrimers cytotoxicity in MNCs from healthy volunteers and for studying the influence of PPI-G4-OS-Mal-III dendrimers on inhibition or induction of MNCs lymphocytes proliferation, as well as on erythrocyte hemolysis and on platelets (PLT) aggregation. Isolation of mononuclear cells (MNCs), cell cultures, also assessment of apoptosis and cytotoxicity were made using the same methods as in the Example 1.

In the studies, the results obtained for the PPI-G4-OS-Mal-III dendrimers of the general formula I, in which 25%, 30%, 40% or 45% R substituents stand for maltotriose residues (the remaining R substituents being H) were of the same character as the results obtained for the dendrimer tested in Example 2.

As described above, PPI-G4-OS-Mal-III dendrimer supplementation to CLL lymphocytes significantly induces the mechanism of apoptosis in those cells, thus considerably reducing their proliferation and survival. It has been proven that one may expect an effective therapeutic effect in treating proliferative neoplastic diseases, particularly chronic lymphocytic leukemia (CLL), using the tested PPI-G4-OS-Mal-III dendrimer as a the therapeutically active substance. At the same time, it has been proven that the tested PPI-G4-OS-Mal-III dendrimer administered via i.v. route in the way presented in the invention, is non-toxic to other morphotic elements of blood (erythrocytes, platelets), which ensures its safe use in humans.

TABLE 5

The influence of PPI-G4-OS-Mal-III (25%) dendrimer and FA on CLL cells (MEC-1) in vitro.

| | Control | | | PPI-G4-OS-Mal-III (25%) (4 mg) | | | PPI-G4-OS-Mal-III (25%) (8 mg) | | | FA 1.6 μM | | | Statistical Analysis (P value) |
|---|---|---|---|---|---|---|---|---|---|---|---|---|---|
| | 1 Ann+ IP− | 2 Ann+ IP+ | 3 Ann− IP+ | 4 Ann+ IP− | 5 Ann+ IP+ | 6 Ann− IP+ | 7 Ann+ IP− | 8 Ann+ IP+ | 9 Ann− IP+ | 10 Ann+ IP− | 11 Ann+ IP+ | 12 Ann− IP+ | 13 |
| | | | | | | 24 h | | | | | | | |
| n | 11 | 11 | 11 | 11 | 11 | 11 | 11 | 11 | 11 | 11 | 11 | 11 | 1 vs 4 = 0.001 |
| X | 4.10 | 4.36 | 11.38 | 8.11 | 32.14 | 10.14 | 8.70 | 37.70 | 11.93 | 3.82 | 6.51 | 14.78 | 2 vs 5 < 0.001 |
| SD | 2.22 | 2.10 | 3.58 | 2.05 | 8.20 | 3.53 | 3.01 | 8.22 | 6.66 | 2.02 | 1.98 | 3.19 | 3 vs 6 = 0.01 |
| CAI (%) | | | | | 31.79 | | | 37.94 | | | 1.87 | | 1 vs 7 = 0.001 |
| | | | | | | | | | | | | | 2 vs 8 < 0.001 |
| | | | | | | | | | | | | | 3 vs 9 < 0.09 |
| | | | | | | | | | | | | | 2 vs 11 = 0.023 |
| | | | | | | | | | | | | | 3 vs 12 = 0.02 |
| | | | | | | | | | | | | | 4 vs 10 = 0.001 |
| | | | | | | | | | | | | | 5 vs 11 < 0.001 |
| | | | | | | | | | | | | | 7 vs 10 = 0.001 |
| | | | | | | | | | | | | | 8 vs 11 < 0.001 |
| | | | | | | | | | | | | | 9 vs 12 = 0.026 |
| | | | | | | 48 h | | | | | | | |
| n | 11 | 11 | 11 | 11 | 11 | 11 | 11 | 11 | 11 | 11 | 11 | 11 | 2 vs 5 < 0.001 |
| X | 3.70 | 5.13 | 15.65 | 6.30 | 36.99 | 13.39 | 6.59 | 41.71 | 10.15 | 5.55 | 10.26 | 22.82 | 3 vs 6 < 0.001 |
| SD | 1.68 | 4.08 | 3.28 | 6.10 | 10.15 | 7.15 | 4.66 | 7.23 | 6.27 | 3.87 | 3.17 | 4.12 | 2 vs 8 < 0.001 |
| CAI (%) | | | | | 34.46 | | | 39.47 | | | 6.98 | | 3 vs 9 < 0.001 |
| | | | | | | | | | | | | | 2 vs 11 = 0.001 |
| | | | | | | | | | | | | | 3 vs 12 < 0.001 |
| | | | | | | | | | | | | | 5 vs 11 < 0.001 |
| | | | | | | | | | | | | | 6 vs 12 = 0.036 |
| | | | | | | | | | | | | | 8 vs 11 < 0.001 |
| | | | | | | | | | | | | | 9 vs 12 = 0.001 | n—number of samples; X—mean percentage of cells; SD—standard deviation; CAI—compensating apoptotic index
Ann+IP− - early apoptosis; Ann+IP+ - late apoptosis; Ann−IP+ - necrosis;

TABLE 6

The influence of PPI-G4-OS-Mal-III (30%) dendrimer and FA on CLL cells (MEC-1) in vitro.

| | Control | | | PPI-G4-OS-Mal-III (30%) (4 mg) | | | PPI-G4-OS-Mal-III (30%) (8 mg) | | | FA 1.6 μM | | | Statistical Analysis (P value) |
|---|---|---|---|---|---|---|---|---|---|---|---|---|---|
| | 1 Ann+ IP− | 2 Ann+ IP+ | 3 Ann− IP+ | 4 Ann+ IP− | 5 Ann+ IP+ | 6 Ann− IP+ | 7 Ann+ IP− | 8 Ann+ IP+ | 9 Ann− IP+ | 10 Ann+ IP− | 11 Ann+ IP+ | 12 Ann− IP+ | 13 |
| | | | | | | 24 h | | | | | | | |
| n | 4 | 4 | 4 | 4 | 4 | 4 | 4 | 4 | 4 | 4 | 4 | 4 | 1 vs 7 = 0.005 |
| X | 2.58 | 4.88 | 8.18 | 6.30 | 17.83 | 10.53 | 8.50 | 18.18 | 9.65 | 3.98 | 10.83 | 7.68 | 2 vs 8 = 0.001 |
| SD | 0.87 | 1.86 | 4.11 | 3.30 | 7.25 | 4.65 | 2.55 | 3.00 | 1.38 | 1.57 | 1.42 | 2.66 | 3 vs 9 = 0.006 |
| CAI (%) | | | | | 16.67 | | | 19.22 | | | 7.35 | | 3 vs 12 = 0.02 |
| | | | | | | | | | | | | | 7 vs 10 = 0.02 |
| | | | | | | | | | | | | | 8 vs 11 = 0.002 |
| | | | | | | 48 h | | | | | | | |
| n | 4 | 4 | 4 | 4 | 4 | 4 | 4 | 4 | 4 | 4 | 4 | 4 | 3 vs 6 = 0.001 |
| X | 2.60 | 10.85 | 15.15 | 7.63 | 22.00 | 15.23 | 7.10 | 22.73 | 4.93 | 2.70 | 18.55 | 15.00 | 2 vs 8 = 0.02 |
| SD | 1.44 | 2.66 | 2.15 | 4.83 | 19.65 | 6.44 | 3.60 | 3.89 | 9.46 | 1.83 | 2.06 | 6.66 | 3 vs 9 = 0.03 |
| CAI (%) | | | | | 16.18 | | | 16.38 | | | 7.80 | | 3 vs 12 = 0.03 | n—number of samples; X—mean percentage of cells; SD—standard deviation; CAI—compensating apoptotic index
Ann+IP− - early apoptosis; Ann+IP+ - late apoptosis; Ann−IP+ - necrosis;

TABLE 7

The influence of PPI-G4-OS-Mal-III (40%) dendrimer and FA on CLL cells (MEC-1) in vitro.

| | Control | | | PPI-G4-OS-Mal-III (40%) (4 mg) | | | PPI-G4-OS-Mal-III (40%) (8 mg) | | | FA 1.6 μM | | | Statistical |
|---|---|---|---|---|---|---|---|---|---|---|---|---|---|
| | 1 Ann+ IP− | 2 Ann+ IP+ | 3 Ann− IP+ | 4 Ann+ IP− | 5 Ann+ IP+ | 6 Ann− IP+ | 7 Ann+ IP− | 8 Ann+ IP+ | 9 Ann− IP+ | 10 Ann+ IP− | 11 Ann+ IP+ | 12 Ann− IP+ | Analysis (P value) 13 |
| 24 h | | | | | | | | | | | | | |
| n | 4 | 4 | 4 | 4 | 4 | 4 | 4 | 4 | 4 | 4 | 4 | 4 | 1 vs 7 = 0.001 |
| X | 2.58 | 4.88 | 8.18 | 6.30 | 20.83 | 10.53 | 8.50 | 24.18 | 9.67 | 3.98 | 10.83 | 7.68 | 2 vs 8 = 0.002 |
| SD | 0.87 | 1.86 | 4.11 | 3.30 | 7.25 | 4.50 | 2.55 | 3.12 | 1.43 | 1.57 | 1.42 | 2.66 | 3 vs 9 = 0.001 |
| CAI (%) | | | | | 19.67 | | | 25.22 | | | 7.35 | | 3 vs 12 = 0.02 |
| | | | | | | | | | | | | | 7 vs 10 = 0.001 |
| | | | | | | | | | | | | | 8 vs 11 = 0.001 |
| 48 h | | | | | | | | | | | | | |
| n | 4 | 4 | 4 | 4 | 4 | 4 | 4 | 4 | 4 | 4 | 4 | 4 | 3 vs 6 = 0.01 |
| X | 2.60 | 10.85 | 15.15 | 8.13 | 22.00 | 15.23 | 10.12 | 30.73 | 7.95 | 2.70 | 18.55 | 15.00 | 2 vs 8 = 0.03 |
| SD | 1.44 | 2.66 | 2.15 | 4.33 | 19.65 | 6.44 | 3.60 | 3.89 | 9.46 | 1.83 | 2.06 | 6.66 | 3 vs 9 = 0.03 |
| CAI (%) | | | | | 16.68 | | | 27.40 | | | 7.80 | | | n—number of samples; X—mean percentage of cells; SD—standard deviation; CAI—compensating apoptotic index
Ann+IP− - early apoptosis; Ann+IP+ - late apoptosis; Ann−IP+ - necrosis;

TABLE 8

The influence of PPI-G4-OS-Mal-III (45%) dendrimer and FA on CLL cells (MEC-1) in vitro.

Figure 1:
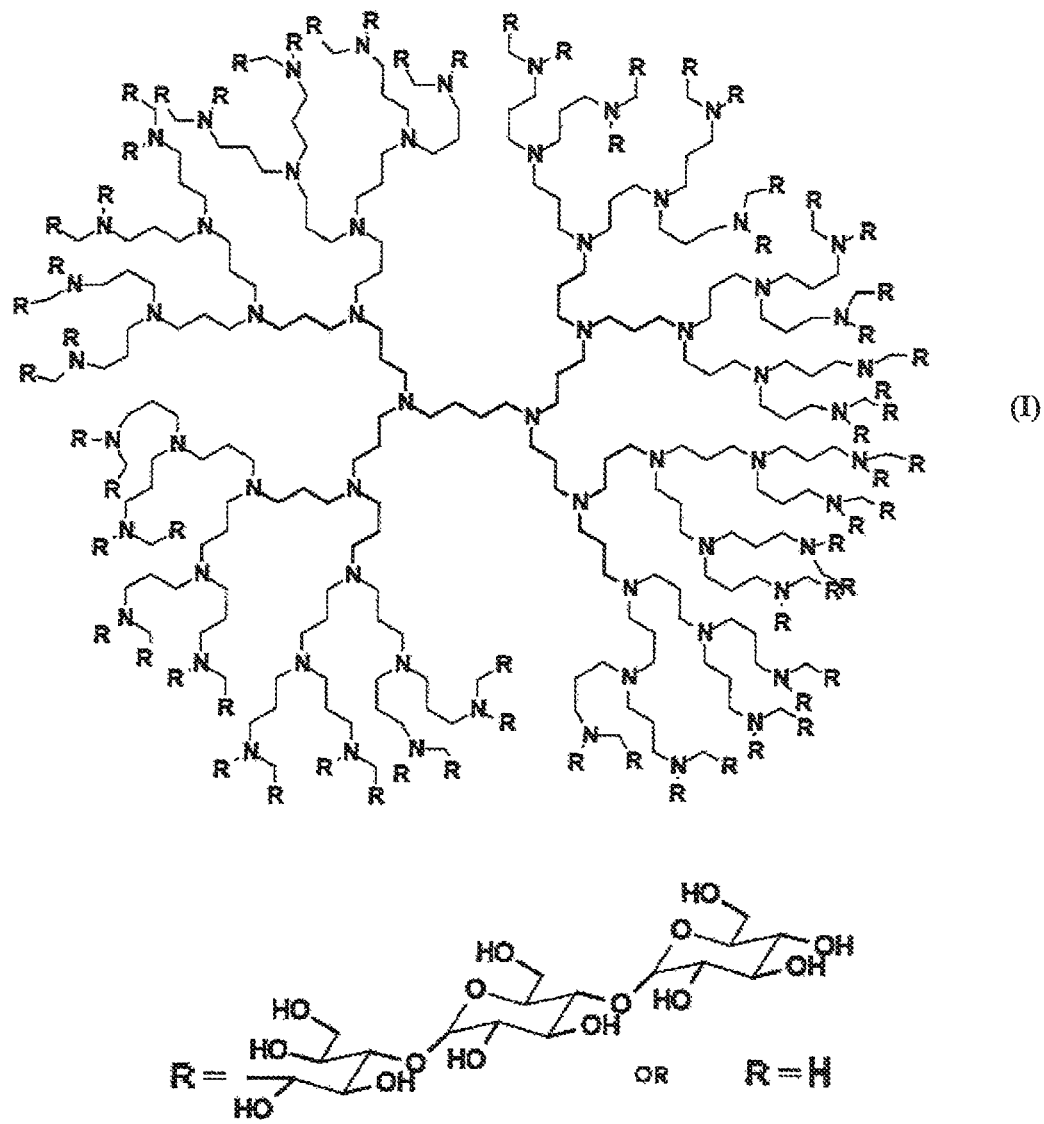
FIG. 1 represents the general formula I of the present dendrimer PPI-G4-OS-Mal-III.
Figure 2:
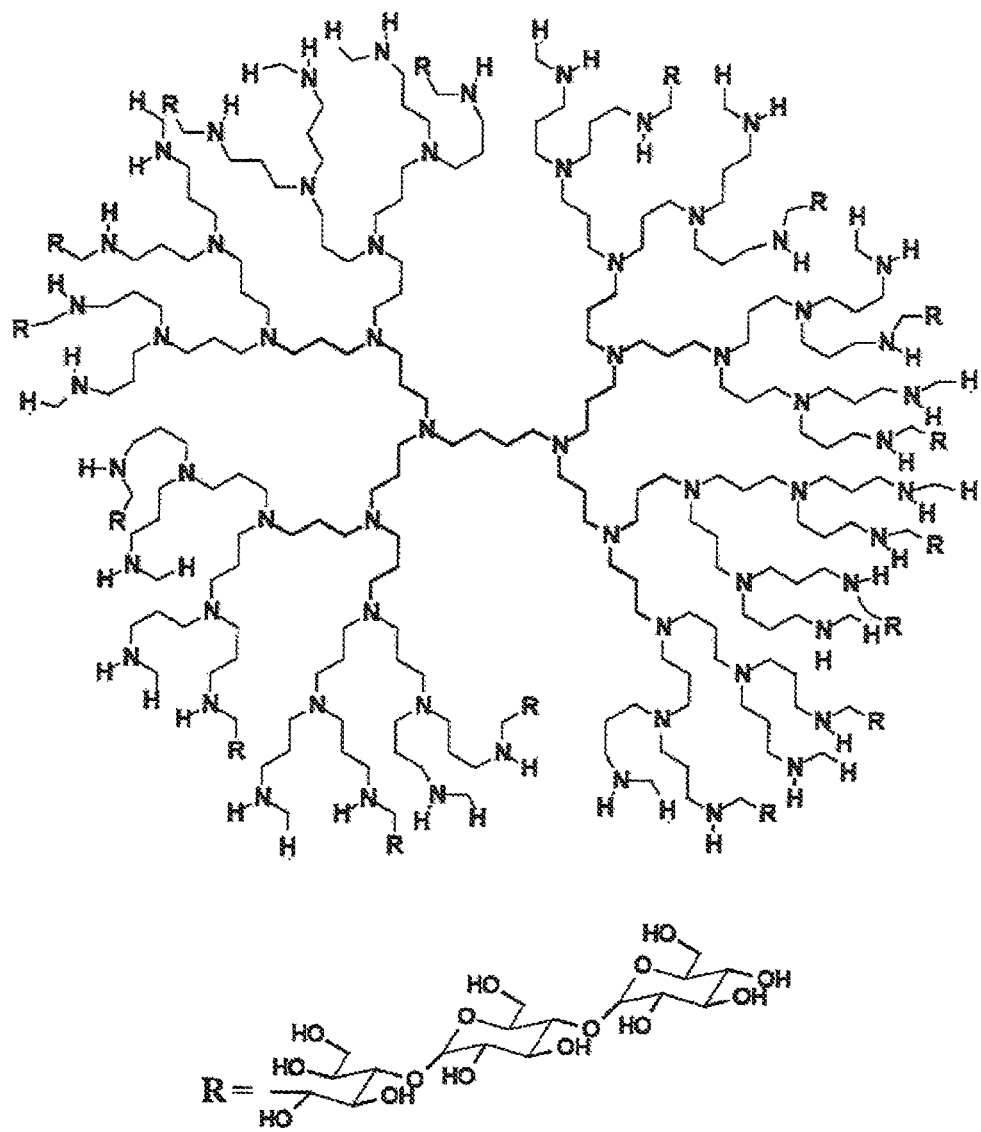
FIG. 2 shows the structure of the dendrimer of general formula I, with the 16 surface maltotriose residues.
Figure 3:
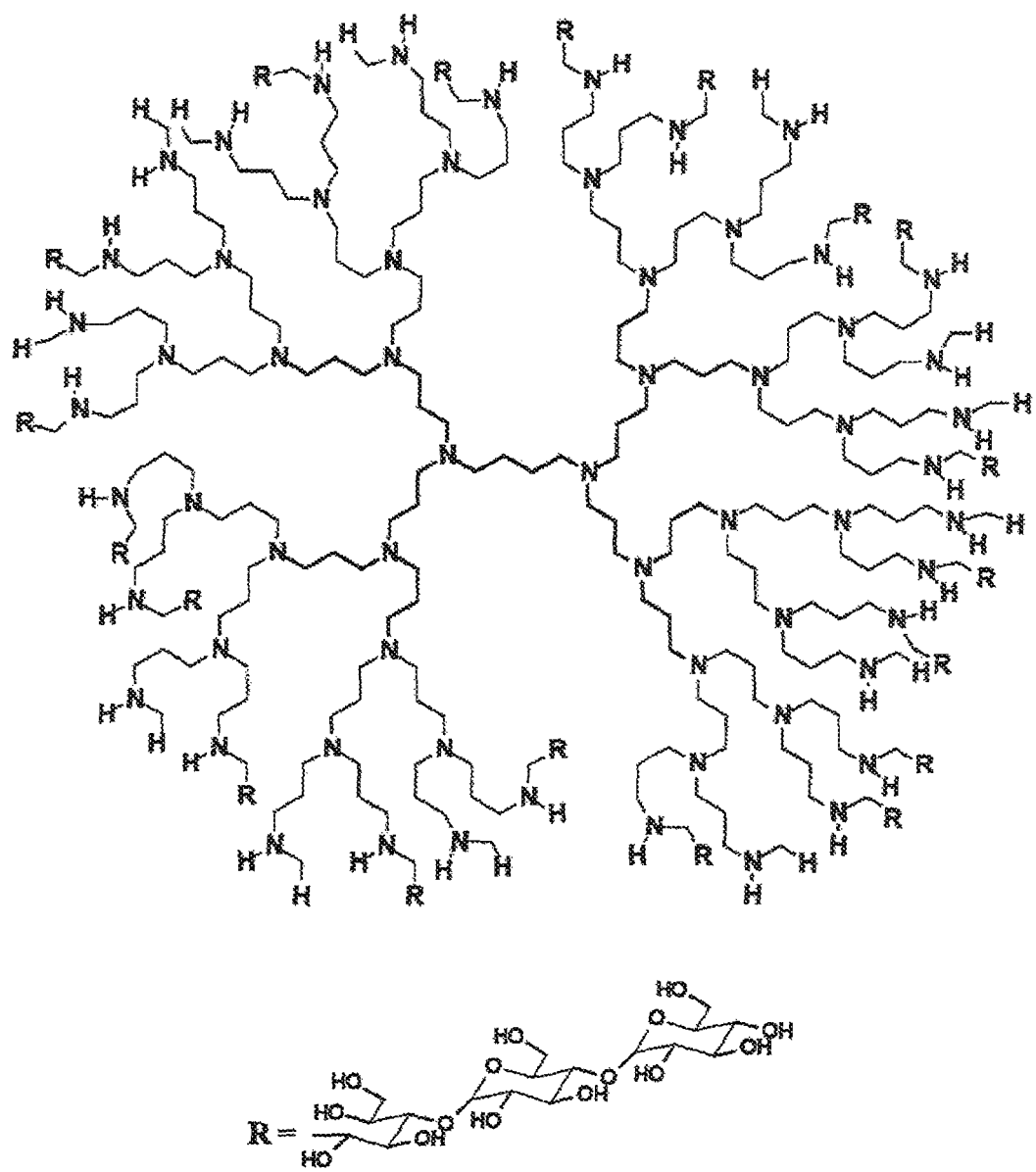
FIG. 3 shows the structure of the dendrimer of general formula I, with the 19 surface maltotriose residues.

| | Control | | | PPI-G4-OS-Mal-III (45%) (4 mg) | | | PPI-G4-OS-Mal-III (45%) (8 mg) | | | FA 1.6 μM | | | Statistical |
|---|---|---|---|---|---|---|---|---|---|---|---|---|---|
| | 1 Ann+ IP− | 2 Ann+ IP+ | 3 Ann− IP+ | 4 Ann+ IP− | 5 Ann+ IP+ | 6 Ann− IP+ | 7 Ann+ IP− | 8 Ann+ IP+ | 9 Ann− IP+ | 10 Ann+ IP− | 11 Ann+ IP+ | 12 Ann− IP+ | Analysis (P value) 13 |
| 24 h | | | | | | | | | | | | | |
| n | 6 | 6 | 6 | 6 | 6 | 6 | 6 | 6 | 6 | 6 | 6 | 6 | 2 vs 5 = 0.001 |
| X | 2.87 | 3.00 | 4.90 | 2.23 | 26.13 | 5.17 | 4.23 | 34.12 | 1.70 | 3.77 | 6.50 | 18.20 | 2 vs 8 < 0.001 |
| SD | 0.70 | 0.79 | 0.36 | 1.97 | 4.18 | 2.37 | 2.32 | 4.36 | 1.25 | 1.85 | 1.84 | 0.17 | 3 vs 9 = 0.013 |
| CAI (%) | | | | | 22.49 | | | 32.48 | | | 4.40 | | 2 vs 11 = 0.022 |
| | | | | | | | | | | | | | 3 vs 12 < 0.001 |
| | | | | | | | | | | | | | 6 vs 12 < 0.001 |
| | | | | | | | | | | | | | 8 vs 11 < 0.001 |
| | | | | | | | | | | | | | 9 vs 12 < 0.001 |
| 48 h | | | | | | | | | | | | | |
| n | 6 | 6 | 6 | 6 | 6 | 6 | 6 | 6 | 6 | 6 | 6 | 6 | 1 vs 4 < 0.001 |
| X | 1.00 | 5.03 | 11.80 | 9.63 | 36.23 | 24.87 | 4.50 | 41.53 | 19.70 | 2.93 | 15.93 | 20.27 | 3 vs 6 = 0.007 |
| SD | 0.36 | 0.32 | 6.09 | 1.65 | 3.01 | 7.58 | 1.25 | 2.07 | 6.46 | 1.95 | 6.90 | 3.93 | 1 vs 7 = 0.01 |
| CAI (%) | | | | | 39.63 | | | 40.02 | | | 12.83 | | 2 vs 8 < 0.001 |
| | | | | | | | | | | | | | 5 vs 11 < 0.001 |
| | | | | | | | | | | | | | 4 vs 10 = 0.01 |
| | | | | | | | | | | | | | 6 vs 12 = 0.01 | n—number of samples; X—mean percentage of cells; SD—standard deviation; CAI—compensating apoptotic index
Ann+IP− - early apoptosis; Ann+IP+ - late apoptosis; Ann−IP+ - necrosis;

The invention claimed is:

1. A method of treating or alleviating a blood neoplastic proliferative disease with an impaired mechanism of apoptosis, in a human in need thereof, comprising administering a therapeutically effective amount of a maltotriose-coated $4^{th}$ generation poly(propyleneimine) dendrimer-PPI-G4-OS-Mal-III of FIG. 1 wherein 25 to 45% of R substituents stand for a maltotriose residue and each of the remaining R substituents is H, comprising the steps:
   a) preparing said maltotriose-coated $4^{th}$ generation poly (propyleneimine) dendrimer—PPI-G4-OS-Mal-III of the general formula I, wherein R has the above defined meaning, in form suitable for i.v. administration, comprising a vehicle or diluent and optionally other suitable biologically active, substances, and
   b) administering intravenously said maltotriose-coated $4^{th}$ generation poly(propyleneimine) dendrimer-PPI-G4-OS-Mal-III of the general formula I, wherein R has the above defined meaning.

2. The method according to claim 1, wherein a therapeutically effective amount of maltotriose-coated $4^{th}$ generation poly(propyleneimine) dendrimer—PPI-G4-OS-Mal-III of FIG. 1, wherein preferably 35% of R substituents stand for a maltotriose residue and each of the remaining R substituents is H, is administered to a human subject.

3. The method according to claim 1, wherein the blood neoplastic proliferative disease with an impaired mechanism of apoptosis is a chronic lymphocytic leukemia in humans.

4. The method according to claim 1, wherein the therapeutically effective amount of said PPI-G4-OS-Mal-III dendrimer is administered together with a physiological saline buffer, such as PBS (phosphate-buffered saline) as a pharmaceutically acceptable solvent suitable for i.v. administration.

5. The method according to claim 4, wherein the pharmaceutically acceptable solvent suitable for i.v. administration further comprises other adjuvants and/or biologically active substances.

* * * * *